(12) United States Patent  (10) Patent No.: US 9,170,172 B2
Hunt et al.  (45) Date of Patent: Oct. 27, 2015

(54) COMPOSITE STRUCTURE HAVING AN EMBEDDED SENSING SYSTEM

(75) Inventors: Jeffrey H. Hunt, Thousand Oaks, CA (US); John H. Belk, Saint Louis, MO (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 13/562,832

(22) Filed: Jul. 31, 2012

(65) Prior Publication Data

US 2013/0048841 A1 Feb. 28, 2013

Related U.S. Application Data

(63) Continuation-in-part of application No. 13/215,969, filed on Aug. 23, 2011, now abandoned.

(51) Int. Cl.
*G01M 11/08* (2006.01)
*G01N 21/84* (2006.01)
*G01B 11/16* (2006.01)

(52) U.S. Cl.
CPC .............. *G01M 11/086* (2013.01); *G01B 11/18* (2013.01); *G01N 2021/8472* (2013.01)

(58) Field of Classification Search
None
See application file for complete search history.

(56) References Cited

U.S. PATENT DOCUMENTS

| 4,936,649 A * | 6/1990 | Lymer ................. G01M 5/0091 156/158 |
| 5,026,140 A | 6/1991 | Russom |
| 5,026,141 A | 6/1991 | Griffiths |
| 5,293,050 A | 3/1994 | Chapple-Sokol et al. |
| 5,299,271 A | 3/1994 | Hildebrand |
| 5,319,435 A | 6/1994 | Melle et al. |
| 5,513,913 A | 5/1996 | Ball et al. |
| 5,627,637 A | 5/1997 | Kapteyn |
| 5,633,748 A | 5/1997 | Perez et al. |

(Continued)

FOREIGN PATENT DOCUMENTS

| WO | WO 98/27406 A1 | 6/1998 |
| WO | WO 98/30881 A1 | 7/1998 |

OTHER PUBLICATIONS

Lee, H.W.H. et al., "Nonlinear Optical Properties and Applications of Silicon and Germanium Quantum Dot Nanocomposites," Nonlinear Optics: Materials, Fundamentals, and Applications, 2000, pp. 12-13.*

(Continued)

*Primary Examiner* — Gordon J Stock, Jr.
(74) *Attorney, Agent, or Firm* — Alston & Bird LLP (57) ABSTRACT

A composite structure having an embedded sensing system is provided, along with corresponding systems and methods for monitoring the health of a composite structure. The composite structure includes composite material and an optical fiber disposed within the composite material. The optical fiber includes a plurality of quantum dots for enhancing its non-linear optical properties. The quantum dots may be disposed in the core, in the cladding and/or on the surface of the optical fiber. The optical fiber is configured to support propagation of the signals and to be sensitive to a defect within the composite material. The quantum dots create a non-linear effect, such as a second order effect, in response to the defect in the composite material. Based upon the detection and analysis of the signals including the non-linear effect created by the quantum dots, a defect within the composite material may be detected.

28 Claims, 7 Drawing Sheets

(56) References Cited

U.S. PATENT DOCUMENTS

| | | | |
|---|---|---|---|
| 5,770,155 A * | 6/1998 | Dunphy et al. | 422/82.05 |
| 6,004,639 A | 12/1999 | Quigley et al. | |
| 6,204,920 B1 | 3/2001 | Ellerbrock et al. | |
| 6,819,845 B2 | 11/2004 | Lee et al. | |
| 6,882,051 B2 | 4/2005 | Majumdar et al. | |
| 6,930,820 B1 | 8/2005 | Shooks, Jr. et al. | |
| 6,978,070 B1 | 12/2005 | McCarthy et al. | |
| 7,005,669 B1 | 2/2006 | Lee | |
| 7,113,660 B2 * | 9/2006 | Andrews et al. | 385/13 |
| 7,132,676 B2 | 11/2006 | Shields et al. | |
| 7,283,693 B2 | 10/2007 | Martin et al. | |
| 7,326,365 B2 | 2/2008 | Bawendi | |
| 7,358,525 B2 | 4/2008 | Lee | |
| 7,362,938 B1 | 4/2008 | Herz et al. | |
| 7,574,074 B1 | 8/2009 | Huang | |
| 7,623,974 B2 | 11/2009 | Cipra | |
| 7,706,650 B2 | 4/2010 | Martin | |
| 8,135,244 B1 | 3/2012 | Sander et al. | |
| 2005/0067559 A1 | 3/2005 | Ogisu et al. | |
| 2005/0231729 A1 | 10/2005 | Lopushansky et al. | |
| 2008/0085086 A1 | 4/2008 | Herz et al. | |
| 2008/0232242 A1 | 9/2008 | Healey et al. | |
| 2009/0092352 A1 * | 4/2009 | Ng et al. | 385/13 |
| 2010/0188652 A1 | 7/2010 | Bianchi et al. | |
| 2010/0237255 A1 | 9/2010 | Monro et al. | |
| 2013/0050685 A1 * | 2/2013 | Hunt et al. | 356/73.1 |

OTHER PUBLICATIONS

Liu, Ansheng et al., "Near-field Optical Second-harmonic Generation in Semiconductor Quantum Dots," Nonlinear Optics 1998: Materials, Fundamentals and Applications, 1998, pp. 376-378.*

Nanomaterialstore.com, selling carbon nanotubes, nanotubes, nanometals, nano-semiconductors, nan . . . dated 2005-2012, [online] [retrieved Aug. 21, 2012]. Retrieved from the Internet: <URL: http://www.nanomaterialstore.com/nano-phosphor.php>. 2 pages.

Extended European Search Report from corresponding European Patent Application No. 12181606.0 dated Sep. 9, 2015.

* cited by examiner

COMPOSITE STRUCTURE HAVING AN EMBEDDED SENSING SYSTEM

CROSS-REFERENCES TO RELATED APPLICATIONS

This application is a continuation-in-part of copending U.S. patent application Ser. No. 13/215,969, filed on Aug. 23, 2011, which is hereby incorporated herein in its entirety by reference.

TECHNOLOGICAL FIELD

Embodiments of the present disclosure relate generally to composite structures and, more particularly, to composite structures having embedded sensing systems for monitoring the health of a composite material.

BACKGROUND

Composite structures are structures consisting of two or more components often with some imparted order which are utilized in a wide variety of applications. For example, air vehicles, such as aircraft, spacecraft or the like, may utilize composite structures in order to take advantage of the benefits attributable to the increased strength-to-weight ratio offered by composite materials. Other applications that may include composite structures include other types of vehicles, such as automobiles, marine vehicles, bicycles and the like, as well as a wide variety of other structures, such as buildings, bridges, etc. Composite structures may also be produced and used with additional functionalities including altered thermal, electrical, acoustical, or mechanical properties by suitably modifying the materials used, the structure itself, or the process used to produce the structure.

Composite structures may be fabricated in various manners designed to impart a predetermined order to a plurality of elements dispersed within a resin or other mostly continuous medium, e.g, polymer, glass, or cement. Typically, a composite structure includes a plurality of structural fibers, such as glass fibers or other elements including carbon fibers, metalized carbon fibers, metal or polymer sheets, carbon or polymer veils, pre-impregnated composite sheets, woven sheets of fibers, matts of random or organized fibers, metal or polymer meshes, embedded in a resin matrix. The resin matrix may be any one of many thermoplastic or thermoset polymer combinations, adhesives or other bonding materials, or cement. Once the composite structure has been laid up, such as by placing a plurality of composite plies one upon another or by laying a plurality of composite tows one beside another, in a manner so as to have the desired shape or woven into a predetermined two dimensional (2D) or three dimensional (3D) structure, the composite structure may be cured, melted or bonded in one or more processing steps.

While composite structures offer a number of advantages, composite structures may occasionally have various anomalies, such as delamination between composite plies, waviness within the composite plies or marcelling in which a composite tow rolls at least partially on top of itself so as to create an inner swirl within the composite structure. While some of these anomalies may be detected from a visual inspection of the composite structure, a number of the anomalies may reside within the interior of the composite structure so as not to be detected during a visual inspection of the composite structure. As such, a variety of inspection techniques utilizing, for example, x-rays, ultrasonic signals or the like have been developed in order to interrogate the interior of a composite structure. While these inspection techniques may detect a number of anomalies, such as ply delaminations, other anomalies that may be created by the misorientation or misplacement of the structural fibers within the resin of a composite structure may present more of a challenge from a detection standpoint.

In this regard, the plurality of structural fibers or other elements within a composite structure generally extends in a predefined direction with the physical properties of the composite structure depending, at least in part, upon the directionality of the structural fibers or other elements. In some instances, however, the structural fibers or other elements within a composite structure may assume a different and an unintended orientation or position which may cause the physical properties of the composite structure to also be different. For example, the structural fibers or other included elements that extend proximate a resin-rich area may migrate or move toward or into the resin-rich area, thereby deviating from their intended orientation. The unintended orientation or position of the structural fibers may be the result of gravity, hydrostatic pressure, chemical or boiling action or mechanical action. Since this deviation in the orientation or position of the structural fibers or other elements may impact the physical properties of the composite structure, it would be desirable to detect such deviations in the orientation or position of the structural fibers or other elements as well as to detect other defects in the composite structure in a reliable manner such that appropriate repairs could be made, if so desired.

BRIEF SUMMARY

A composite structure having an embedded sensing system is provided in accordance with one embodiment to the present disclosure. In this regard, the embedded sensing system may include an optical fiber having a plurality of quantum dots that enhance the non-linear optical properties of the optical fiber. As such, defects or other current or past changes or states (hereinafter generally referred to as "defects") within the composite structure may cause the quantum dots to create a non-linear effect that is readily discernible, thereby providing a reliable indicator of a defect within the composite structure. A system and a method for monitoring the health of a composite structure are also provided according to embodiments to the present disclosure. In this context, the health of a composite structure includes its chemical state, e.g., degree of cure, its mechanical state, e.g. strain field, its environment, e.g., temperature or moisture content, presence of flaws or porosity, e.g., disbonds or ply dislocations, its thermal or electrical properties, or ion density, any of which may have a bearing on the ability of the structure to complete its mission.

In one embodiment, a system for monitoring the health of a composite structure is provided that includes a composite material having a resin and a plurality of structural elements embedded within the resin and an optical fiber disposed within the composite material with the optical fiber including a plurality of quantum dots for enhancing the non-linear optical properties of the optical fiber. In an embodiment in which the optical fiber includes a core and a cladding surrounding the core, the core may include the plurality of quantum dots so to amplify signals propagating through the core and/or enhance the sensitivity of the optical fiber. Additionally or alternatively, the cladding of the optical fiber may include the plurality of quantum dots in order to enhance interaction with the surrounding resin via a fiber evanescent wave. Still further, the plurality of quantum dots may be disposed upon a surface of the optical fiber in order to provide for stronger interaction with the local strain field, material and evanescent wave. The system of this embodiment also includes a signal source configured to provide signals to the optical fiber for propagation therealong. The plurality of quantum dots create a non-linear effect, such as a second order effect, e.g. the generation of a second harmonic, in response to a defect in the composite material. The system of this embodiment also includes a detector configured to detect the signals including the non-linear effect following propagation through the optical fiber. Since the non-linear effect may be readily identified, the system of this embodiment may reliably detect defects in the composite material so as to facilitate further inspection or repair. For example, defects such as deviations in the path of a fiber tow or composite ply may be detected along with, in some embodiments, the location of such defects.

The detector of one embodiment is configured to detect the signals following reflection of the signals. For example, the optical fiber may include a Bragg grating or one or more partially reflecting mirrors for causing reflection of at least some of the signals. In another embodiment in which the optical fiber extends between first and second ends with the signal source positioned proximate the first end of the optical fiber, the system may also include a reflector positioned at the second end of the optical fiber so as to reflect the signals through the optical fiber from the second end toward the first end. In this embodiment, the detector is responsive to signals emitted by the first end of the optical fiber following reflection of the signals therethrough.

In another embodiment, a composite structure is provided that has an embedded sensing system. In this regard, the composite structure includes composite material having a resin and a plurality of structural elements embedded within the resin. The composite structure also includes an optical fiber disposed within the composite material. The optical fiber includes a plurality of quantum dots for enhancing the non-linear optical properties of the optical fiber. In an embodiment into which the optical fiber includes a core and a cladding surrounding the core, the core may include the plurality of quantum dots so to amplify signals propagating through the core and/or enhance the sensitivity of the optical fiber. Additionally or alternatively, the cladding of the optical fiber may include the plurality of quantum dots in order to enhance interaction with the surrounding resin via a fiber evanescent wave. Still further, the plurality of quantum dots may be disposed upon a surface of the optical fiber in order to provide for stronger interaction with the local strain field, material and evanescent wave. The optical fiber of this embodiment is configured to support propagation of the signals therealong and to be sensitive to a defect within the composite material. In this regard, the plurality of quantum dots create a non-linear effect, such as a second order effect, e.g., the generation of a second harmonic, in response to the defect in the composite material. In one embodiment, the optical fiber may include a Bragg grating or a partially reflecting mirror for reflecting at least a portion of the optical signals.

In a further embodiment, a method for monitoring the health of a composite structure is provided. The method includes providing a composite structure including a composite material having a resin and a plurality of structural elements embedded within the resin as well as an optical fiber disposed within the composite material with the optical fiber having a plurality of quantum dots for enhancing the non-linear optical properties of the optical fiber. In an embodiment in which the optical fiber includes a core and a cladding surrounding the core, the core may include the plurality of quantum dots so to amplify signals propagating through the core and/or enhance the sensitivity of the optical fiber. Additionally or alternatively, the cladding of the optical fiber may include the plurality of quantum dots in order to enhance interaction with the surrounding resin via a fiber evanescent wave. Still further, the plurality of quantum dots may be disposed upon a surface of the optical fiber in order to provide for stronger interaction with the local strain field, material and evanescent wave. The method also includes providing signals to the optical fiber for propagation therealong, such as from a first end of the optical fiber to an opposed second end. The method of one embodiment also includes creating a non-linear effect, such as a second order effect, e.g., the generation of a second harmonic, with the plurality of quantum dots in response to a defect in the composite material. The method of this embodiment also detects the signals, including the non-linear effect, following propagation through the optical fiber. Since the non-linear effect may be readily identified, the method of this embodiment may reliably detect defects the composite material so as to facilitate further inspection or repair.

In one embodiment in which the signal source is positioned proximate the first end of the optical fiber, the method may also include reflecting the signals through the optical fiber from the second end toward the first end from which the signals were initially launched. In this embodiment, the detection of the signals may include detecting the signals emitted by the first end of the optical fiber following reflection of the signals therethrough.

In accordance with embodiments of the present disclosure, systems, methods and composite structures are provided in order to reliably identify defects within a composite material so as to permit further inspection or repair to be performed in an informed and efficient manner. However, the features, functions and advantages that have been discussed may be achieved independently and the various embodiments of the present disclosure may be combined in other embodiments, further details of which may be seen with reference to the detailed description and drawings.

BRIEF DESCRIPTION OF THE DRAWINGS

Having thus described the example embodiments of the present disclosure in general terms, reference will now be made to the accompanying drawings, which are not necessarily drawn to scale, and wherein:

DETAILED DESCRIPTION

Embodiments of the present disclosure now will be described more fully hereinafter with reference to the accompanying drawings, in which some, but not all embodiments are shown. Indeed, these embodiments may be embodied in many different forms and should not be construed as limited to the embodiments set forth herein; rather, these embodiments are provided so that this disclosure will satisfy applicable legal requirements. Like numbers refer to like elements throughout.

Figure 1:
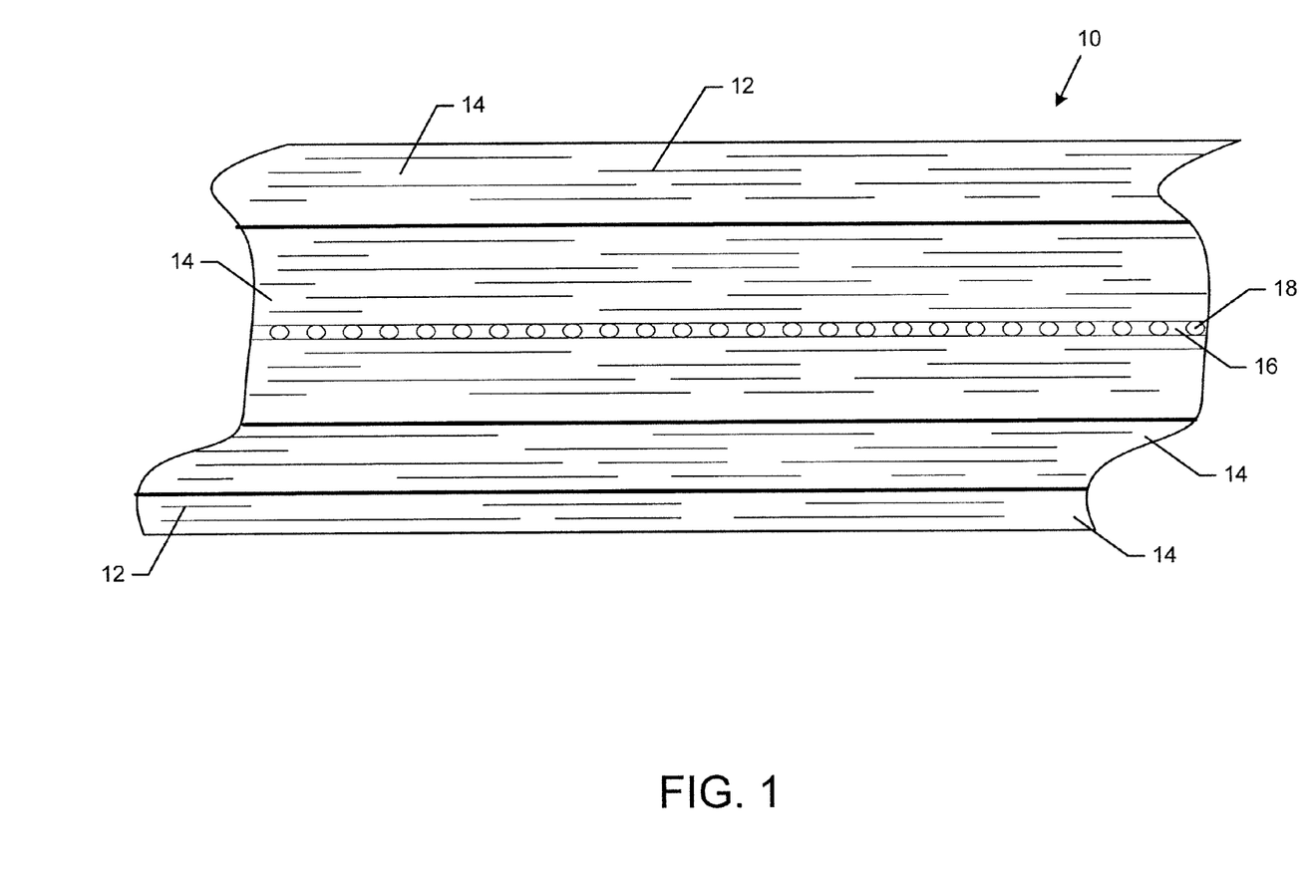
FIG. 1 is a cross-sectional representation of a composite structure in accordance with one embodiment of the present disclosure which illustrates a composite material and an embedded sensing system, including an optical fiber having a plurality of quantum dots that is disposed within the composite material.

Referring now to FIG. 1, a composite structure 10 having an embedded sensing system in accordance with one embodiment of the present disclosure is illustrated. The composite structure 10 may be utilized in a variety of applications including in air vehicles, such as aircraft, spacecraft or the like, land vehicles, such as automobiles, trucks, trailers, bicycles, etc., marine vehicles, buildings and other structures. As shown in FIG. 1, the composite structure 10 includes a composite material having a plurality of structural elements 12 embedded within a matrix of resin 14. The composite material may include a number of different types of structural elements 12 including structural fibers such as glass fibers, carbon fibers or the like and other elements such as graphene sheets, a carbon veil, a woven prepreg, a solid sheet and a metal or polymer mesh. Additionally, the composite material may include a number of different types of resin 14 including, for example, epoxy resin, polyester resin or the like.

In the illustrated embodiment, the composite material includes a plurality of composite plies, each having the plurality of structural elements 12 embedded within the matrix of resin 14. The composite plies may be laid one upon the other as shown in FIG. 1. However, the composite material may be fabricated in other manners including, for example, a plurality of composite tows that are laid beside one another or by including sheets, veils, pre-impregnated cloth, metal or polymer mesh or the like. During the fabrication of the composite material, the composite material is laid up or formed so as to have a desired shape, such as by laying the composite plies or composite tows or other elements upon a mandrel or tool having the desired shape. During the formation of the composite material, such as during the lay up or placement of the plurality of composite plies, composite tows or the like, and prior to curing of the composite material, one or more optical fibers 16 including a plurality of quantum dots 18 is disposed within the composite material, such as by being embedded within the composite material, as also shown in FIG. 1. In this regard, the optical fiber 16 is disposed within the composite material in such a manner that at least one end of the optical fiber and, more typically, both of the opposed ends of the optical fiber are accessible, such as by extending to an edge, such as opposed edges, of the composite material. While a single optical fiber 16 is shown in FIG. 1, the composite structure 10 may include a plurality of optical fibers which may, in one embodiment, extend parallel to one another through the composite material.

The optical fiber 16 may be positioned between composite plies, composite tows, or the like. Once the optical fiber 16 has been disposed within the composite material, the composite material may be cured or otherwise processed to solidify the resin 14 such that the composite material retains the shape in which the composite plies or composite tows were laid up. This curing or other solidification of the composite material also serves to secure the optical fiber 16 within the composite material such that the optical fiber extends therethrough.

The optical fiber 16 that is disposed within the composite material includes a plurality of quantum dots 18. While a plurality of quantum dots 18 are shown within the optical fiber 16 of FIG. 1, the quantum dots are illustrated to be larger than typical for purposes of illustration, but not of example. The optical fiber 16 of one embodiment is formed to include the quantum dots 18 by implanting spectroscopically enhancing features within the optical fiber or by inducing microscopic structural changes within the optical fiber which cause enhancements to the hyperpolarizability of the optical fiber. As described below, the plurality of quantum dots 18 enhance the non-linear optical properties of the optical fiber 16 relative to a comparable optical fiber that does not include quantum dots.

In regards to the implantation of spectroscopically enhancing features or the inducement of microscopic structural changes within the optical fiber, it is noted that spectroscopic enhancement in the case of nonlinear optics diverges somewhat from the traditional linear case. In linear spectroscopy, light will be more readily absorbed by a material when the light frequency matches that associated with a material excitation. Once that light is absorbed, it may be re-emitted or thermalized within the material, depending on the rest of the material parameters.

In the nonlinear case, it is not necessary for all or any of the light input frequencies to coincide with material excitations to produce a spectroscopic enhancement of the effect in question. In one case, for example, there may be two inputs, one of which is resonant with a material parameter, and the other not resonant. At the sum-frequency of the two inputs, there will be an enhancement of the efficiency of sum-frequency production, even though there is no absorption, per se, in the material. In another case, neither of the two inputs may coincide with a material excitation, but if the frequency difference coincides with a material excitation, the efficiency of light production at the difference frequency will be enhanced. Alternately, the case of second harmonic generation may have an input signal that is not resonant, but if the second harmonic frequency coincides with a material excitation, the second harmonic generation process will be enhanced.

There will be naturally occurring material excitations associated with any optical fiber or quantum dot materials. As such, the input frequencies to the optical fiber may be selected to allow the nonlinear processes to be resonant with one of more of the material excitations. For example, if there are two distinct input frequencies $v_1$ and $v_2$, then $v_1$ can be resonant, or $v_2$ can be resonant, or $v_1+v_2$ can be resonant, or $v_1-v_2$ can be resonant with one or more of the material parameters. Additionally, several of the combinations may be resonant simultaneously. In the second harmonic case, there is a single frequency input at $v_1$ with either $v_1$ being resonant or $2v_1$ ($v_1+v_1$) being resonant. Alternately, the optical fiber with the quantum dots can be doped with materials that provide a material resonance. The material with which the optical fiber is doped could be, but is not limited to, atomic or molecular species that have known spectral features.

Alternately, microscopic structural changes not involving material excitations can lead to nonlinear signal enhancements. In this regard, a fiber that is physically strained will have local molecular bonds strained. In this regard, it has been established that straining molecular bonds will increase their nonlinear response through a larger hyperpolarizibility. In addition, a physically strained material will have a net orientation introduced at a molecular level which will also increase the net cumulative effect of the hyperpolarizibility. The combination of these two effects will lead to a larger nonlinear optical response, even if pure spectroscopic enhancements are unavailable.

Figure 2:
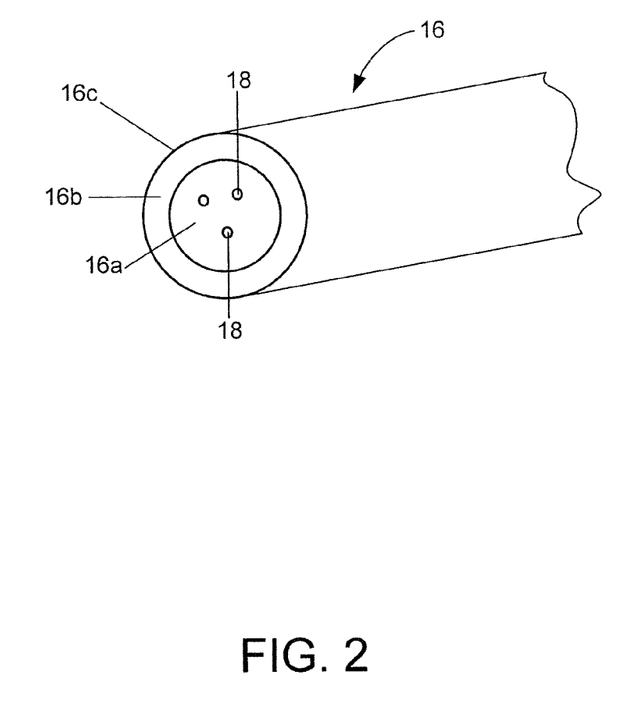
FIG. 2 is a fragmentary perspective view of an optical fiber in accordance with one embodiment of the present disclosure.

The optical fiber 16 may include quantum dots 18 in one or more regions of the optical fiber. As shown in FIG. 2, for example, the optical fiber 16 of one embodiment may include a core 16a surrounded by cladding 16b having a different coefficient of refraction than the core so as to largely confine the signals propagating through the core within the core. In the illustrated embodiment, the quantum dots 18 are included within the core 16a of the optical fiber 16. In this embodiment, the quantum dots 18 within the core 16a of the optical fiber 16 may serve to amplify signals propagating through the core of the optical fiber and to enhance the sensitivity of the optical fiber to defects within the composite material. In an alternative embodiment, the optical fiber 16 may include quantum dots at the interface between the core 16a and the cladding 16b. In yet another embodiment, the optical fiber 16 may include the quantum dots 18 within the cladding 16b, thereby enhancing the interaction of the signals propagating through the optical fiber with the surrounding composite material via fiber evanescent waves. In a further embodiment, the optical fiber 16 may include a plurality of quantum dots 18 on the outer surface 16c of the optical fiber, such as the outer surface of the cladding. In this embodiment, the plurality of quantum dots 18 disposed upon the outer surface of the optical fiber 16 may interact more strongly with the local strain field in the composite material via evanescent waves. The optical fiber 16 may include the plurality of quantum dots 18 in only one of these regions, that is, only one of the core 16a, the cladding 16b or the outer surface 16c of the optical fiber. Alternatively, the optical fiber 16 may include the plurality of the quantum dots 18 in any two of these regions, such as any two of the core 16a, the cladding 16b or the outer surface 16c of the optical fiber or, in some embodiments, may include the plurality of quantum dots in all three of these regions, that is, in each of the core, the cladding, and the outer surface of the optical fiber.

In another embodiment, the optical fiber 16 may be a gradient index fiber that includes quantum dots 18 such that reference herein to the core of an optical fiber including quantum dots is also intended to encompass the embodiment in which a gradient index fiber includes quantum dots. In yet another embodiment, the optical fiber 16 may be a light pipe having a hollow core for supporting the propagation of infrared (IR) or other signals therealong. In this embodiment, the optical fiber 16 may also include a plurality of quantum dots 18. For example, the plurality of quantum dots 18 may be disposed upon an inner surface of the light pipe that faces and defines the hollow core. Although several types of optical fibers 16 are described above, the foregoing examples are not meant to be all inclusive and other types of optical fibers may be employed including elliptical core optical fibers, multi-hole optical fibers, multi-core optical fibers and optical fibers having a myriad of other internal or surface structures that can impact the environment of any nearby quantum dots disposed within or on the optical fiber.

Regardless of type of optical fiber 16 and/or the region(s) of the optical fiber that includes the quantum dots 18, the optical fiber may include quantum dots in a relatively uniform manner along its length or may only include quantum dots in one or more discrete segments along the length of the optical fiber. In this regard, the optical fiber 16 may be more sensitive to defects in the composite material that are proximate to a segment of the optical fiber that includes quantum dots 18 relative to a segment of the optical fiber that does not include quantum dots.

Figure 3:
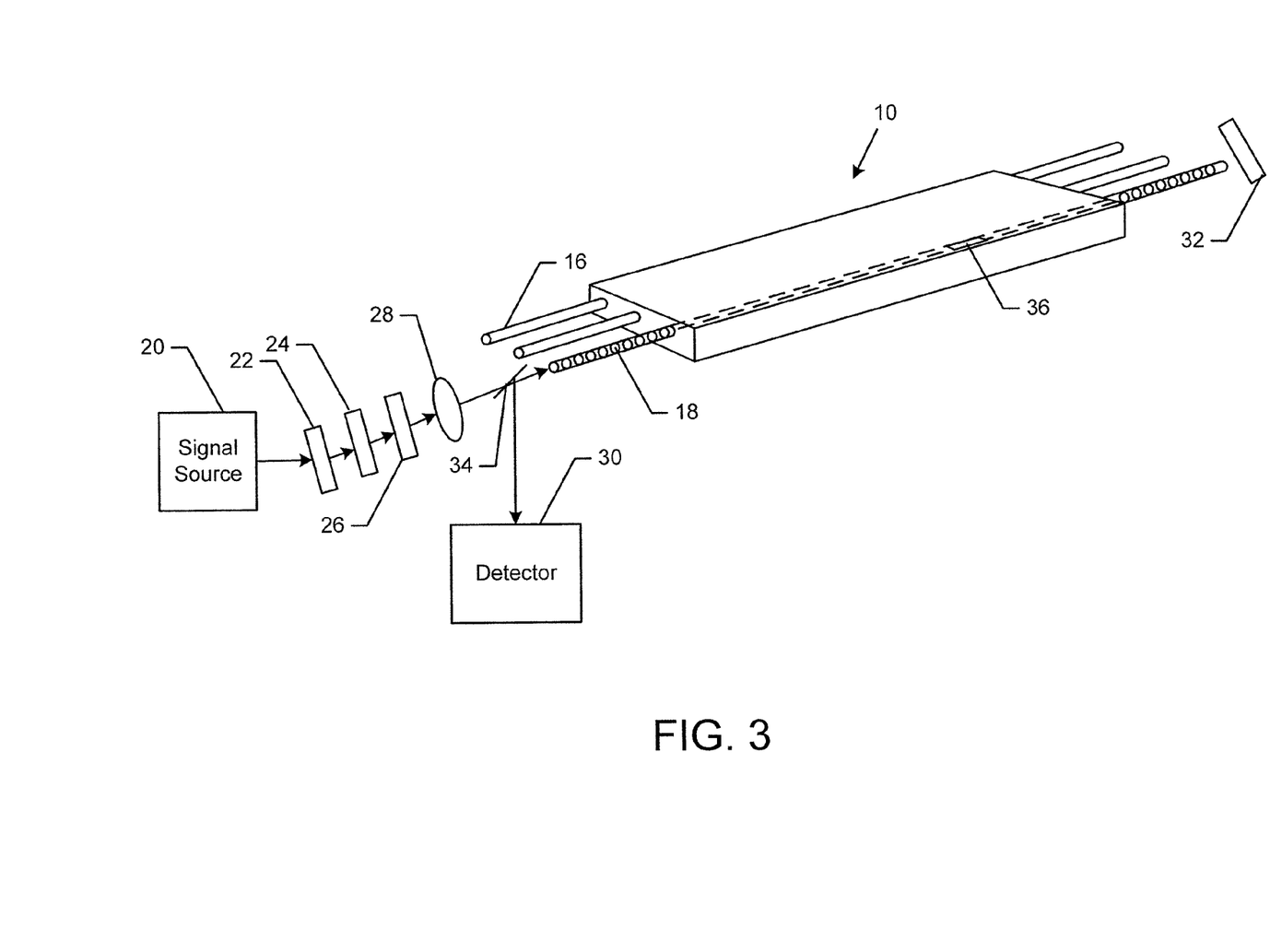
FIG. 3 is a schematic representation of a system for monitoring the health of a composite structure in accordance with one embodiment of the present disclosure.

As noted above and as shown in more detail in FIG. 3, at least one end of the optical fiber 16 and, more typically, both of the opposed first and second ends of the optical fiber are accessible, such as by extending beyond or at least to an edge of a composite material. As shown in FIG. 3, a system in accordance with one embodiment to the present disclosure not only includes the composite structure 10 including the composite material and the embedded optical fiber 16, but also includes a signal source 20, such as an optical source, for providing signals to the optical fiber for propagation therealong. In this regard, the signal source 20 may be configured to introduce signals via the first end of the optical fiber 16 for propagation along the length of the optical fiber toward the second end of the optical fiber. Although the system may include various types of signal sources 20 for introducing various types of signals for propagation along the optical fiber, the signal source of one embodiment is a laser, such as a pulsed laser, for providing laser signals to the optical fiber 16 for propagation therethrough. In another embodiment in which the optical fiber 16 is a light pipe, the signal source 20 may be an IR signal source for providing IR signals to the first end of the optical fiber.

The signal source 20 may provide the signals directly to the optical fiber 16, such as to the first end of the optical fiber. As shown in FIG. 3, however, the signals generated by the signal source may be conditioned prior to being delivered to the optical fiber 16. For example, the system may include a wavelength selection device 22, such as a wavelength filter, for filtering the signals generated by the signal source 20 to insure that signals having only one or more predefined frequencies or a predefined range of frequency pass through the wavelength selection device for delivery to the optical fiber 16. The system may also include a polarization device 24, such as a Glan Taylor prism, a Glan Thompson prism, a Wollaston prism, a thin film polarizer, in combination with waveplates, including thin film devices or optically active materials, such as quartz, for limiting the signals that propagate beyond the polarization device to those having one or more predefined polarizations. Further, the system may include an intensity filter 26, such as a neutral density filter, a color filter, variable attenuation devices such as wedge pairs or matched prisms, or other fixed or variable optical attenuation devices, for limiting the energy carried by the signals that are to be provided to the optical fiber 16 to ensure that the optical fiber is not damaged by signals having excessively high energy levels. Although the system of the illustrated embodiment includes each of the wavelength selection device 22, the polarization sensitive device 24 and the intensity filter 26, the system may include any one or any combination of these elements in other embodiments. As shown in FIG. 3, the system may also include an optical device 28, such as a lens, for focusing the signals upon the first end of the optical fiber 16, such as by matching the signals to the numerical aperture of the optical fiber.

As also shown in FIG. 3, the system also includes a detector 30 configured to receive the signals including any non-linear effects generated from the signals following propagation through the optical fiber 16, such as following fabrication of the composite structure 10 such that the composite structure is as-cured or during the fabrication of the composite structure so as to provide in-process monitoring. In one embodiment, the detector 30 may be positioned so as to receive the signals exiting from the second end of the optical fiber 16, opposite the first end into which the signals from the signal source 20 are introduced into the optical fiber. In the illustrated embodiment, however, the system is configured such that the signals are reflected and returned to the first end of the optical fiber 16. As such, the detector 30 of this embodiment may be positioned so as to receive the signals as well as non-linear effects created by the signals upon their exit from the first end of the optical fiber 16. By constructing the system such that the detector 30 receives reflected signals from the first end of the optical fiber 16, a majority of the components of the system may be co-located, thereby potentially simplifying the design and installation of the components.

As shown in FIG. 3, a beam splitter 34 may be positioned to receive the reflected signals and to redirect the reflected signals that exit the first end of the optical fiber 16 to the detector 30. By including the beam splitter 34, the detector 30 may receive the signals exiting the first end of the optical fiber 16 even though the detector is offset or out of linear alignment with the optical fiber, thereby facilitating the introduction of the signals from the signal source 20 into the first end of the optical fiber without being obstructed by the detector. The system may include various types of detectors including a solid state detector, such as a photodiode. The detector may be formed of a material that is selected and based upon the wavelength of the signals to be detected since, for example, semiconductor photodiodes generally detect signals having a predefined range of wavelengths that can be absorbed by the semiconductor material. In one embodiment, a silicon photodiode may be utilized to detect the returning signals and the associated non-linear effects. In order to provide for increased sensitivity, such as to facilitate detection of the non-linear effects which may be smaller than the reflected signals, the detector may include an avalanche photodiode (APD).

The signals propagating along the optical fiber 16 may be reflected in various manners. For example, the system may include a reflector 32, such as a mirror, for receiving the signals reaching the second end of the optical fiber 16 and for reflecting the signals such that the signals and the associated non-linear effects are returned to the optical fiber and propagate from the second end toward the first end for receipt and detection by the detector 30. Additionally, or alternatively, the optical fiber 16 may include a Bragg grating 36 or other types of reflectors such as partially reflecting mirrors, e.g., a Fabry-Perot etalon having one or more partially reflecting mirrors, formed within the optical fiber, such as described in U.S. Pat. No. 5,682,237, for reflecting at least a portion of the signals and the associated non-linear effects that are propagating along the optical fiber. In an instance in which the optical fiber 16 includes a partially reflecting mirror, quantum dots 18 may be disposed on or within the mirror in one embodiment.

In accordance with an embodiment of the present disclosure, defects within the composite material may affect the signals propagating along the optical fiber 16, such as by altering the magnitude and/or phase of the signals. For example, defects in the composite material that cause the optical fiber 16 to be bent or to otherwise subject the optical fiber to stress or strain, such as due to displacement of the structural elements 14 within the composite material, ply waviness, marcelling or like, may cause a change in the signals propagating along the optical fiber. By detecting the signal following propagation through the optical fiber 16 and by identifying any changes in the signal, defects within the composite material may be identified. For example, defects involving the deviation of in the path of a fiber tow or the position of a composite ply may be identified based upon the signals returning from the optical fiber 16 in accordance with one embodiment of the present disclosure.

Some defects within the composite material may not only alter the properties of the optical signals propagating along the optical fiber 16, but may also cause the signals, or at least some of the signals, to be reflected. As such, the detector 30 of this embodiment may not simply detect the signals that return to the first end of the optical fiber 16, but may also determine the time at which the reflected signals return to the first end of the optical fiber. By determining the time difference between the time at which the signals were launched into the first end of the optical fiber 16 and the time at which the reflected signals exited from the first end of the optical fiber as well as the speed at which the signals propagate through the optical fiber, the detector 30 and/or an associated time domain reflectometer (TDR) may determine the relative location along the length of the optical fiber at which the defect is located, thereby directing further inspection of the composite material and/or repair of the composite material to the location in question.

As described above, the optical fiber 16 includes a plurality of quantum dots 18. The plurality of the quantum dots 18 create a non-linear effect in response to a defect in the composite material. For example, the quantum dots may create a variety of non-linear effects including a second order effect, such as the generation of a second harmonic. In this regard, the second order effects, such as a generation of a second harmonic, that is generated by the plurality of quantum dots 18 of one embodiment may be strongly affected by the lack of centrosymmetry caused by the presence of defects within the composite material, such as by defects occasioned by changes in the placement and positioning of the structural elements 14. Additionally, or alternatively, the quantum dots may generate a third order effect, such as the generation of a third order harmonic. Quantum dots have nonlinear optical responses that are inherently nonlinear. Because of their small physical dimensions, and because their optical refractive index will differ from the surrounding media, there will be a local field enhancement of any light signal that propagates in their vicinity. Since nonlinear effects are dependent on light intensity, the local field enhancement caused by the quantum dots will increase the size of any nonlinear response. In addition to third harmonic generation, other enhanced effects may include parametric amplification, Raman scattering, and four wave mixing. In general, second order nonlinear effects are not allowed in centro-symmetric media. But the straining of the composite structure, coupled with the presence of the quantum dots, can break the material symmetry, allowing second order effects such as second harmonic generation, sum-frequency, and difference frequency generation. As such, by including a plurality of quantum dots 18 within the optical fiber 16, the non-linear effects created in response to a defect in the composite material, such as a defect that causes an unanticipated bending of the optical fiber, may serve as a reliable and discernable indicator of the defect. These non-linear effects may also propagate through the optical fiber 16 and be detected by the detector 30. Indeed, the non-linear effects created by the plurality of quantum dots 18 may be of a magnitude that is sufficient to be readily identifiable by the detector 30 and to thereby serve as a reliable indicator of the defect within the composite material. Further, the detector 30 may readily identify the non-linear effects since the non-linear effects are less likely to be adversely impacted by noise, which may impair the detection and evaluation of the primary signals, particularly in instances having a relatively low signal to noise ratio (SNR).

Figure 4:
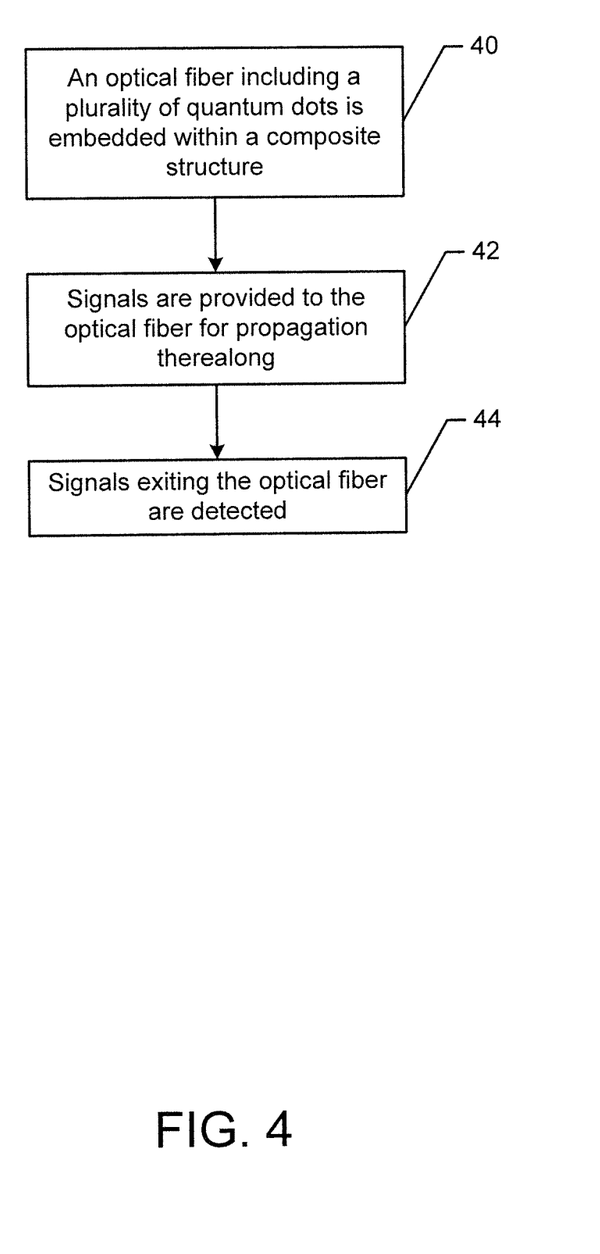
FIGS. 4-6 are flow charts of methods in accordance with embodiments of the present disclosure.
Figure 5:
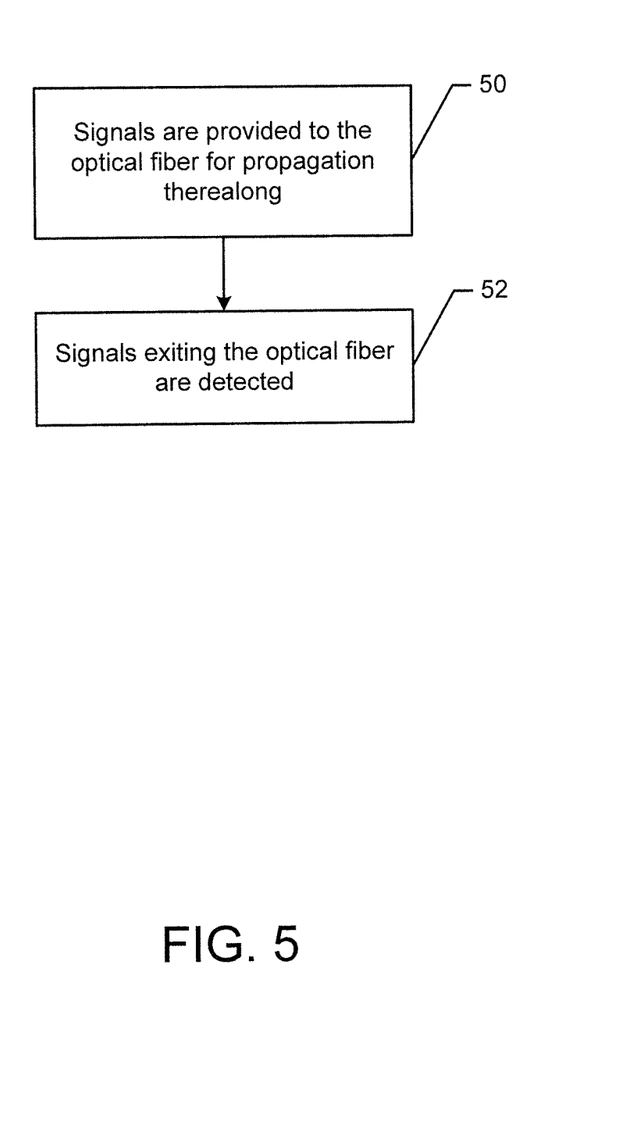
Figure 6:
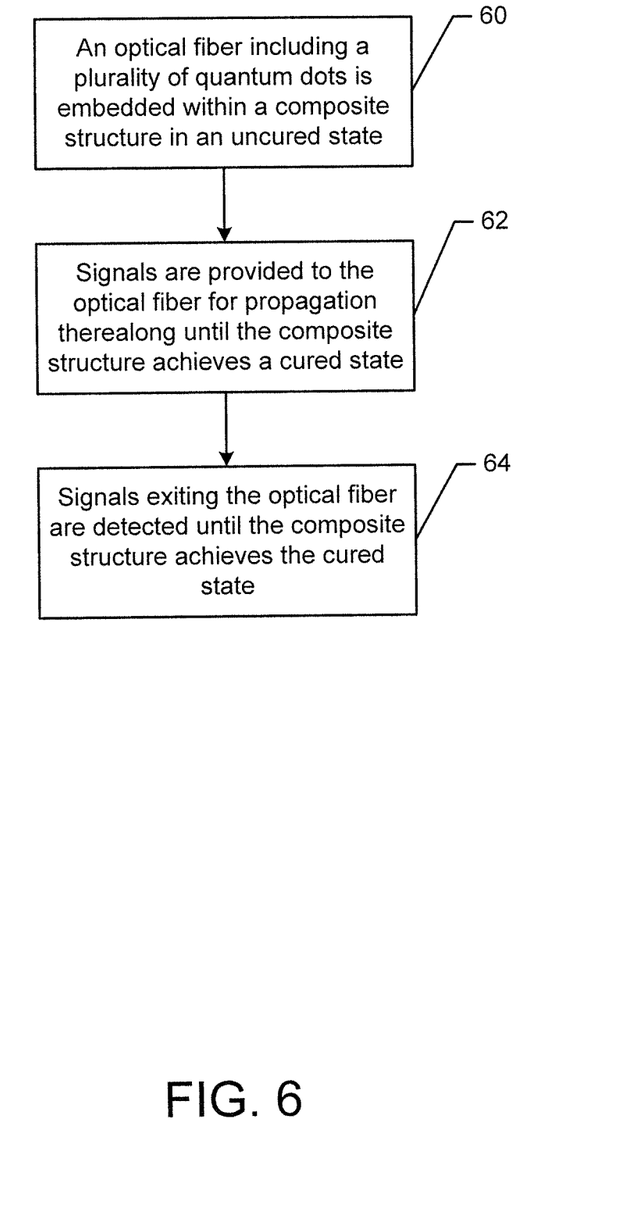

Various methods may be provided in accordance with example embodiments of the present disclosure. As shown in block 40 of FIG. 4, an optical fiber 16 including a plurality of quantum dots 18 may be embedded within a composite structure 10. Once the optical fiber 16 has been embedded in the composite structure 10, signals may be provided to the optical fiber for propagation therealong. See block 42. Signals exiting the optical fiber 16 may then be detected. See block 44. Similarly, FIG. 5 depicts a method in which signals are provided to an optical fiber 16 that is embedded within a composite structure 10 for propagation therealong. See block 50. The optical fiber 16 includes a plurality of quantum dots 18. Signals exiting the optical fiber 16 may then be detected. See block 52. In addition to or instead of employing the method in conjunction with composite materials that have been cured, embodiments of the method may be employed in conjunction with a composite structure 10 in an uncured state. As shown in block 60 of FIG. 6, for example, an optical fiber 16 including a plurality of quantum dots 18 may be embedded within a composite structure 10 in an uncured state. Once the optical fiber 16 has been embedded in the composite structure 10, signals may be provided to the optical fiber for propagation therealong until the composite structure achieves a cured state. See block 62. Signals exiting the optical fiber 16 may then be detected until the composite structure 10 achieves the cured state. See block 64.

Figure 7:
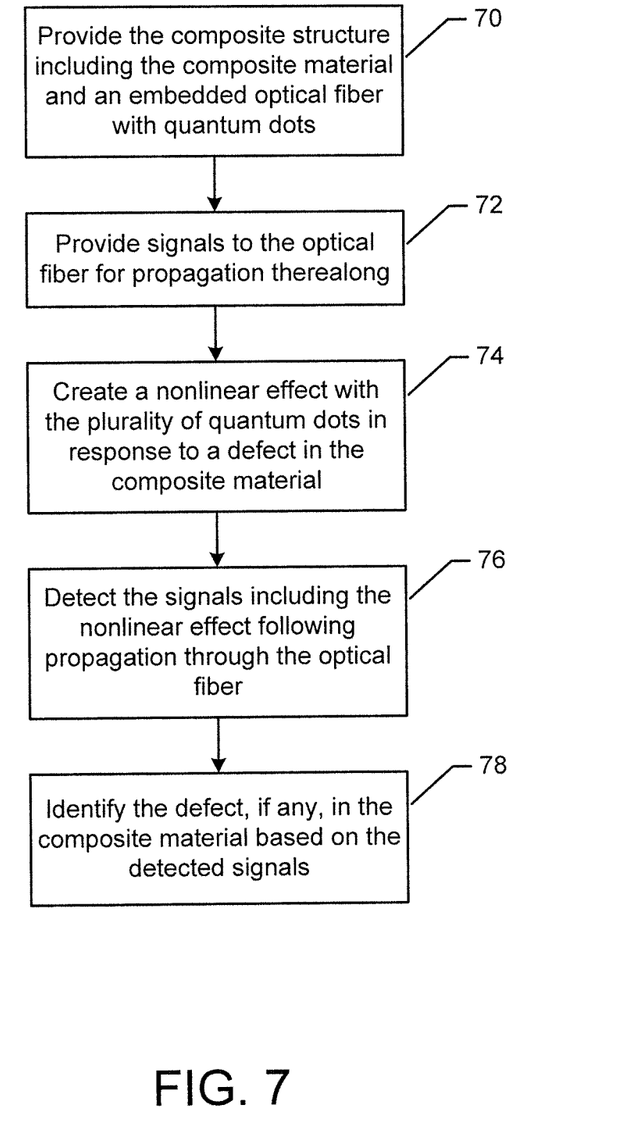
FIG. 7 is a flow chart of a method for monitoring the health of a composite structure in accordance with one embodiment of the present disclosure.

By way of further explanation, a method may therefore be provided for monitoring the health of a composite structure 10 as shown, for example, in the flowchart of FIG. 7. While the health of the composite structure 10 may be monitored following its fabrication, such as in an as-cured state, the system and method of embodiments of the present disclosure may monitor the health of the composite structure during its fabrication prior to curing or other solidification of the resin, thereby providing in-process monitoring. Indeed, the system and method of one embodiment could monitor a composite structure that did not cure or solidify in order to monitor the orientation of the plies or fiber tows. In this regard, the composite structure 10 including a composite material and one or more optical fibers 16 disposed within the composite material may be provided, as shown in operation 70 of FIG. 7. The optical fiber 16 includes a plurality of quantum dots 18 for enhancing the non-linear optical properties of the optical fiber. As shown in operation 72, signals may then be provided to the optical fiber 16 for propagation therealong, such as from a first end into which the signals are introduced toward an opposed second end. In response to a defect in the composite material, such as a defect that may cause the optical fibers to bend in an unanticipated manner or to otherwise result in unanticipated amounts of stress or strain being placed upon the optical fibers, a non-linear effect may be created by the plurality of quantum dots 18 as shown in operation 74. Various non-linear effects may be created including the creation of a second order effect, such as a generation of a second harmonic, the creation of a third order effect, such as a generation of a third order harmonic, or the like in response to the defect in the composite material. The method may also detect signals, including the non-linear effect following propagation through the optical fiber 16, as shown in operation 76. By analyzing the signals including the non-linear effect, such as by means of the detector 30 or a computer associated with and responsive to the detector, instances in which the composite material has a defect that has altered the signals propagating through the optical fiber 16 and has created non-linear effects may be identified. See operation 78. With respect to the defects that may be detected, deviations in the path of a fiber tow and deviations in the position or path of a composite ply may be detected in accordance with one embodiment of the present disclosure. Additionally, the location of the defect may also be determined, such as based upon TDR, in some embodiments. Based upon the detection of a potential defect within the composite material, the method of one embodiment may provide for further testing and analysis of the potential defect and/or for making appropriate repairs to the composite material so as to repair the defect.

In this regard, the signals and the associated non-linear effects that are detected may be compared, such as by the detector 30 or an associated computer, to the signals and associated non-linear effects that are otherwise expected to be detected following propagation of the signal through the optical fiber 16 in an instance in which the composite material does not include any defects. In an instance in which the signals and/or the non-linear effects deviate, such as by at least a predetermined amount or percentage, the method may identify a potential defect within the composite material so as to allow for more detailed analysis and/or repair of the composite material or to inform the user of the need to alter the mission.

By enhancing the non-linear properties of the optical fiber 16 by the inclusion of a plurality of quantum dots 18, the impact of a defect within the composite material on the signals propagating through the optical fiber is correspondingly enhanced. In this regard, the non-linear effects created by the plurality of quantum dots 18 in response to a defect within the composite material are sufficiently repeatable and of a magnitude that may be reliably identified by a detector 30. Thus, the system and method of one embodiment may facilitate the detection of a defect within a composite material so as to permit the composite material to be further analyzed or inspected and/or to promote more focused repair of the composite material in a timely manner or otherwise respond to the new knowledge. Indeed, the analysis of the non-linear effects created by the plurality of quantum dots 18 in response to a defect in the composite material may permit defects to be identified in a reliable manner that is not limited by the relatively low signal to noise ratio that may otherwise impair an analysis that is simply based upon the reflected signals within the optical fiber 16 without consideration of the associated non-linear effects.

As indicated above, the health of a composite material may be monitored by embedding a plurality of optical fibers 16, such as an array of optical fibers, that include quantum dots 18 within the composite material. The signals and associated non-linear effects that are detected by detector 30 following signal propagation through the array of optical fibers may provide multi-dimensional data, such as two dimensional (2D) or three dimensional (3D) data indicative of the health of the composite material by providing, for example, an indication of deviations in the location of a fiber tow or composite ply and, in some embodiments utilizing optical time domain reflectometry, the location of such deviations. In one embodiment, the detector 30 may be configured to display a visual representation of this multi-dimensional data, such as by overlaying a visual representation of the multi-dimensional data onto a model of the composite structure 10 that is being fabricated such that the model can provide a reference for the multi-dimensional data gathered by the system of this embodiment of the present disclosure.

Many modifications and other embodiments set forth herein will come to mind to one skilled in the art to which these embodiments pertain having the benefit of the teachings presented in the foregoing descriptions and the associated drawings. Therefore, it is to be understood that the embodiments are not to be limited to the specific ones disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions other than those explicitly described above are also contemplated as may be set forth in some of the appended That which is claimed:

1. A system for monitoring a composite structure, the system comprising:
    an optical fiber extending between opposed first and second ends with at least a portion of the optical fiber within the composite structure, the optical fiber including a plurality of quantum dots;
    a signal source proximate the first end of the optical fiber and coupled to the optical fiber to provide optical signals to the optical fiber for propagation therealong, wherein the signal source is configured to provide optical signals having first and second distinct input frequencies $v_1$ and $v_2$ with at least one of $v_1+v_2$ or $v_1-v_2$ being resonant with a material excitation of the optical fiber;
    a reflector positioned in optical communication with the optical fiber so as to reflect the optical signals through the optical fiber toward the first end; and
    a detector coupled to the optical fiber to detect optical signals that exit the optical fiber from the first end of the optical fiber following reflection of the signals therethrough,
    wherein the plurality of quantum dots create non-linear properties including at least one of a second order harmonic or a third order harmonic in response to an anomaly in the composite structure that is detectable upon analysis of the optical signals that exit the optical fiber.

2. A system according to claim 1 wherein the optical fiber comprises a core and a cladding surrounding the core, and wherein the core comprises the plurality of quantum dots.

3. A system according to claim 1 wherein the optical fiber comprises a core and a cladding surrounding the core, and wherein the cladding comprises the plurality of quantum dots.

4. A system according to claim 1 wherein the plurality of quantum dots are disposed upon a surface of the optical fiber.

5. A system according to claim 1 wherein the reflector comprises at least one of a Bragg grating or a Fabry-Perot etalon comprising one or more partially reflecting mirrors.

6. A system according to claim 1 wherein the reflector is positioned at the second end of the optical fiber so as to reflect the signals through the optical fiber from the second end toward the first end.

7. A system according to claim 1 further comprising the composite structure in which the optical fiber is embedded, wherein the composite structure is in an uncured state during the propagation of signals along the optical fiber and detection of signals that exit the optical fiber such that the system provides for in-process monitoring of the composite structure during fabrication prior to curing or solidification of a resin of the composite structure.

8. A system according to claim 1 wherein the optical fiber is positioned between composite plies or composite tows that form the composite structure prior to curing or solidification of a resin of the composite structure.

9. A system according to claim 1 wherein the plurality of quantum dots create non-linear properties including at least the third order harmonic in response to an anomaly in the composite structure that is detectable upon analysis of the optical signals that exit the optical fiber.

10. A method for monitoring a composite structure, the method comprising:
    embedding an optical fiber that extends between opposed first and second ends with at least a portion of the optical fiber being within the composite structure, the optical fiber including a plurality of quantum dots;
    providing optical signals to the first end of the optical fiber for propagation therealong, wherein providing optical signals comprises providing optical signals having first and second distinct input frequencies $v_1$ and $v_2$ with at least one of $v_1+v_2$ or $v_1-v_2$ being resonant with a material excitation of the optical fiber;
    reflecting optical signals through the optical fiber toward the first end with a reflector positioned in optical communication with the optical fiber; and
    detecting optical signals that exit the optical fiber from the first end of the optical fiber following reflection of the signals therethrough,
    wherein detecting the optical signals comprises analyzing the optical signals that exit the optical fiber to detect non-linear properties including a second order harmonic or a third order harmonic created by the plurality of quantum dots in response to an anomaly in the composite structure.

11. A method according to claim 10 wherein the optical fiber comprises a core and a cladding surrounding the core, and wherein the core comprises the plurality of quantum dots.

12. A method according to claim 10 wherein the optical fiber comprises a core and a cladding surrounding the core, and wherein the cladding comprises the plurality of quantum dots.

13. A method according to claim 10 wherein the plurality of quantum dots are disposed upon a surface of the optical fiber.

14. A method according to claim 10 wherein steps of embedding the optical fiber, providing signals to the optical fiber and detecting signals that exit the optical fiber are performed while the composite structure is in an uncured state such that the method provides for in-process monitoring of the composite structure during fabrication prior to curing or solidification of a resin of the composite structure.

15. A method according to claim 10 wherein embedding the optical fiber comprises positioning the optical fiber between composite plies or composite tows that form the composite structure prior to curing or solidification of a resin of the composite structure.

16. A method according to claim 10 wherein detecting the optical signals further comprises analyzing the optical signals that exit the optical fiber to detect non-linear properties including the third order harmonic created by the plurality of quantum dots in response to an anomaly in the composite structure.

17. A method for monitoring a composite structure having an optical fiber embedded therein, the optical fiber extending between opposed first and second ends and including a plurality of quantum dots, the method comprising:
    providing optical signals to the first end of the optical fiber for propagation therealong, wherein providing optical signals comprises providing optical signals having first and second distinct input frequencies $v_1$ and $v_2$ with at least one of $v_1+v_2$ or $v_1-v_2$ being resonant with a material excitation of the optical fiber;
    reflecting optical signals through the optical fiber toward the first end with a reflector positioned in optical communication with the optical fiber; and
    detecting optical signals that exit the optical fiber from the first end of the optical fiber following reflection of the signals therethrough,
    wherein detecting the optical signals comprises analyzing the optical signals that exit the optical fiber to detect non-linear properties including a second order harmonic or a third order harmonic created by the plurality of quantum dots in response to an anomaly in the composite structure.

18. A method according to claim 17 wherein the optical fiber comprises a core and a cladding surrounding the core, and wherein the core comprises the plurality of quantum dots.

19. A method according to claim 17 wherein the optical fiber comprises a core and a cladding surrounding the core, and wherein the cladding comprises the plurality of quantum dots.

20. A method according to claim 17 wherein the plurality of quantum dots are disposed upon a surface of the optical fiber.

21. A method according to claim 17 wherein steps of providing signals to the optical fiber and detecting signals that exit the optical fiber are performed while the composite structure is in an uncured state such that the method provides for in-process monitoring of the composite structure during fabrication prior to curing or solidification of a resin of the composite structure.

22. A method according to claim 17 wherein the optical fiber is positioned between composite plies or composite tows that form the composite structure prior to curing or solidification of a resin of the composite structure.

23. A method according to claim 17 wherein detecting the optical signals further comprises analyzing the optical signals that exit the optical fiber to detect non-linear properties including the third order harmonic created by the plurality of quantum dots in response to an anomaly in the composite structure.

24. A method for monitoring a composite structure during manufacture thereof, the method comprising:
    embedding an optical fiber that extends between opposed first and second ends within the composite structure in an uncured state, the optical fiber including a plurality of quantum dots, wherein embedding the optical fiber comprises embedding the optical fiber between composite plies or composite tows that form the composite structure prior to curing or solidification of a resin of the composite structure;
    providing optical signals to the first end of the optical fiber for propagation therealong until the composite structure achieves a cured state, wherein providing optical signals comprises providing optical signals having first and second distinct input frequencies $v_1$ and $v_2$ with at least one of $v_1+v_2$ or $v_1-v_2$ being resonant with a material excitation of the optical fiber;
    reflecting optical signals through the optical fiber toward the first end with a reflector positioned in optical communication with the optical fiber;
    creating a nonlinear effect including at least a second order harmonic or a third order harmonic with the plurality of quantum dots in response to an anomaly in the composite structure; and
    detecting optical signals including the nonlinear effect that exit the optical fiber from the first end of the optical fiber following reflection of the signals therethrough until the composite structure achieves the cured state in order to provide for in-process monitoring of the composite structure during fabrication of the composite structure that commences prior to curing or solidification of the resin of the composite structure.

25. A method according to claim 24 wherein the optical fiber comprises a core and a cladding surrounding the core, and wherein the core comprises the plurality of quantum dots.

26. A method according to claim 24 wherein the optical fiber comprises a core and a cladding surrounding the core, and wherein the cladding comprises the plurality of quantum dots.

27. A method according to claim 24 wherein the plurality of quantum dots are disposed upon a surface of the optical fiber.

28. A method according to claim 24 wherein creating the nonlinear effect comprises creating the nonlinear effect including at least the third order harmonic with the plurality of quantum dots in response to an anomaly in the composite structure.

* * * * *